(12) United States Patent
Whitman (10) Patent No.: US 6,443,973 B1
(45) Date of Patent: *Sep. 3, 2002

(54) ELECTROMECHANICAL DRIVER DEVICE FOR USE WITH ANASTOMOSING, STAPLING, AND RESECTING INSTRUMENTS

(75) Inventor: Michael P. Whitman, New Hope, PA (US)

(73) Assignee: Power Medical Interventions, Inc., New Hope, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/324,452

(22) Filed: Jun. 2, 1999

(51) Int. Cl.$^7$ ............................................. A61B 17/068
(52) U.S. Cl. ................................... 606/219; 227/176.1
(58) Field of Search .............................. 606/219, 170, 606/167, 171, 75; 227/176.1, 179

(56) References Cited

U.S. PATENT DOCUMENTS

| | | |
|---|---|---|
| 3,079,606 A | 3/1963 | Bobrov et al. |
| 3,193,165 A | 7/1965 | Akhalaya et al. |
| 3,256,875 A | 6/1966 | Tsepelev et al. |
| 3,388,847 A | 6/1968 | Kasulin et al. |
| 3,490,675 A | 1/1970 | Green et al. |
| 3,494,533 A | 2/1970 | Green et al. |
| 3,552,626 A | 1/1971 | Astafiev et al. |
| 3,618,842 A | 11/1971 | Bryan |
| 3,662,939 A | 5/1972 | Bryan |
| 3,815,476 A | 6/1974 | Green et al. |
| 3,858,577 A | 1/1975 | Bass et al. |
| 3,859,986 A | 1/1975 | Okada et al. |
| 4,071,029 A | 1/1978 | Richmond et al. |
| 4,085,756 A | 4/1978 | Weaver |
| 4,198,960 A | 4/1980 | Utsugi |
| 4,198,982 A | 4/1980 | Fortner et al. |
| 4,202,479 A | 5/1980 | Razgulov et al. |
| 4,207,898 A | 6/1980 | Becht |
| 4,250,873 A | 2/1981 | Bonnet |
| 4,273,109 A | 6/1981 | Enderby |
| 4,273,111 A | 6/1981 | Tsukaya |
| 4,286,585 A | 9/1981 | Ogawa |
| 4,289,131 A | 9/1981 | Mueller |

(List continued on next page.)

FOREIGN PATENT DOCUMENTS

| | | |
|---|---|---|
| DE | 33 00 768 | 7/1984 |
| EP | 0 116 220 | 8/1984 |
| EP | 0 156 774 | 10/1985 |
| EP | 0 216 532 | 4/1987 |
| EP | 0 399 701 | 11/1990 |
| EP | 0 552 050 | 7/1993 |
| EP | 0 593 920 | 4/1994 |
| GB | 2 044 108 | 10/1980 |
| GB | 2180455 | 4/1987 |
| NL | 77 11 347 | 4/1979 |
| WO | WO 90/05491 | 5/1990 |
| WO | WO 92/16141 | 10/1992 |

*Primary Examiner*—Eduardo C. Robert
(74) *Attorney, Agent, or Firm*—Dann, Dorfman, Herrell and Skillman, P.C.

(57) ABSTRACT

An electromechanical driver for use in gastrointestinal tract surgery, including a flexible sheath and a handle, is provided. Also disclosed are a series of surgical attachments which may be utilized in conjunction with the electromechanical driver. The handle of the driver includes at least one motor which is selectively engageable by the actuation of a trigger. The motor is coupled to a flexible drive shaft which extends through the flexible sheath. At a distal end of the flexible sheath, and correspondingly at the end of the drive shaft, the various surgical attachments may be coupled. The turning of the drive shaft provides the necessary power to actuate the surgical instrument.

42 Claims, 6 Drawing Sheets

U.S. PATENT DOCUMENTS

| | | |
|---|---|---|
| 4,289,133 A | 9/1981 | Rothfuss |
| 4,304,236 A | 12/1981 | Conta et al. |
| 4,310,115 A | 1/1982 | Inoue |
| 4,319,576 A | 3/1982 | Rothfuss |
| 4,351,466 A | 9/1982 | Noiles |
| 4,367,729 A | 1/1983 | Ogiu |
| 4,379,457 A | 4/1983 | Gravener et al. |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,473,077 A | 9/1984 | Noiles et al. |
| 4,476,863 A | 10/1984 | Kanshin et al. |
| 4,485,817 A | 12/1984 | Swiggett |
| 4,487,270 A | 12/1984 | Huber |
| 4,488,523 A | 12/1984 | Shichman |
| 4,489,724 A | 12/1984 | Arnegger |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,520,817 A | 6/1985 | Green |
| 4,534,420 A | 8/1985 | Goldelius |
| 4,559,928 A | 12/1985 | Takayama |
| B1 4,319,576 A | 2/1986 | Rothfuss |
| 4,573,468 A | 3/1986 | Conta et al. |
| 4,574,806 A | 3/1986 | McCarthy |
| 4,576,167 A | 3/1986 | Noiles |
| 4,580,712 A | 4/1986 | Green |
| 4,589,412 A | 5/1986 | Kensey |
| 4,589,582 A | 5/1986 | Bilotti |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,610,383 A | 9/1986 | Rothfuss et al. |
| 4,631,052 A | 12/1986 | Kensey |
| 4,644,952 A | 2/1987 | Patipa et al. |
| 4,646,745 A | 3/1987 | Noiles |
| 4,667,673 A | 5/1987 | Li |
| 4,671,445 A | 6/1987 | Barker et al. |
| 4,672,961 A | 6/1987 | Davies |
| 4,674,515 A | 6/1987 | Andou et al. |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,732,156 A | 3/1988 | Nakamura |
| 4,733,118 A | 3/1988 | Mihalko |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,771,774 A | 9/1988 | Simpson et al. |
| 4,776,506 A | 10/1988 | Green |
| 4,781,186 A | 11/1988 | Simpson et al. |
| 4,817,847 A | 4/1989 | Redtenbacher et al. |
| 4,819,632 A | 4/1989 | Davies |
| 4,867,158 A | 9/1989 | Sugg |
| 4,873,977 A | 10/1989 | Avant et al. |
| 4,887,599 A | 12/1989 | Muller |
| 4,890,602 A | 1/1990 | Hake |
| 4,893,613 A | 1/1990 | Hake |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,928,699 A | 5/1990 | Sasai |
| 4,930,494 A | 6/1990 | Takehana et al. |
| 4,936,845 A | 6/1990 | Stevens |
| 4,955,882 A | 9/1990 | Hakky |
| 4,957,499 A | 9/1990 | Lipatov et al. |
| 4,962,877 A | 10/1990 | Hervas |
| 4,976,688 A | 12/1990 | Rosenblum |
| 4,976,710 A | 12/1990 | Mackin |
| 4,994,060 A | 2/1991 | Rinl et al. |
| 4,995,877 A | 2/1991 | Ams et al. |
| 5,005,749 A | 4/1991 | Aranyi |
| 5,059,203 A | 10/1991 | Husted |
| 5,077,506 A | 12/1991 | Krause |
| 5,104,025 A | 4/1992 | Main et al. |
| 5,133,359 A | 7/1992 | Kedem |
| 5,133,713 A | 7/1992 | Huang et al. |
| 5,133,729 A | 7/1992 | Sjostrom |
| 5,139,513 A | 8/1992 | Segato |
| 5,171,251 A | 12/1992 | Bregen et al. |
| 5,192,292 A | 3/1993 | Cezana et al. |
| 5,197,649 A | 3/1993 | Bessler et al. |
| 5,201,325 A | 4/1993 | McEwen et al. |
| 5,201,750 A | 4/1993 | Höcherl et al. |
| 5,205,459 A | 4/1993 | Brinkerhoff et al. |
| 5,207,697 A | 5/1993 | Carusillo et al. |
| 5,237,884 A | 8/1993 | Seto |
| 5,249,583 A | 10/1993 | Mallaby |
| 5,258,007 A | 11/1993 | Spetzler et al. |
| 5,261,877 A | 11/1993 | Fine et al. |
| 5,267,997 A | 12/1993 | Farin et al. |
| 5,268,622 A | 12/1993 | Philipp |
| 5,269,794 A * | 12/1993 | Rexroth ..................... 606/180 |
| 5,271,543 A | 12/1993 | Grant et al. |
| 5,271,544 A | 12/1993 | Fox et al. |
| 5,275,322 A | 1/1994 | Brinkerhoff et al. |
| 5,285,945 A * | 2/1994 | Brinkerhoff et al. ........ 227/179 |
| RE34,556 E * | 3/1994 | Sjostrom et al. ............ 606/170 |
| 5,289,963 A | 3/1994 | McGarry et al. |
| 5,290,299 A | 3/1994 | Fain et al. |
| 5,292,053 A | 3/1994 | Bilotti et al. |
| 5,312,023 A | 5/1994 | Green et al. |
| 5,318,221 A | 6/1994 | Green et al. |
| 5,326,013 A | 7/1994 | Green et al. |
| 5,333,773 A | 8/1994 | Main et al. |
| 5,350,104 A | 9/1994 | Main et al. |
| 5,383,880 A | 1/1995 | Hooven |
| 5,395,033 A | 3/1995 | Byrne et al. |
| 5,411,508 A | 5/1995 | Bessler et al. |
| 5,431,673 A * | 7/1995 | Summers et al. ........... 606/170 |
| 5,433,721 A | 7/1995 | Hooven et al. |
| 5,467,911 A | 11/1995 | Tsuruta et al. |
| 5,482,197 A | 1/1996 | Green et al. |
| 5,518,163 A | 5/1996 | Hooven |
| 5,518,164 A | 5/1996 | Hooven |
| 5,533,661 A | 7/1996 | Main et al. |
| 5,653,374 A * | 8/1997 | Young et al. ............ 227/176.1 |
| 5,662,673 A | 9/1997 | Kieturakis |
| 5,667,517 A | 9/1997 | Hooven |
| 5,779,130 A * | 7/1998 | Alesi et al. .............. 227/176.1 |
| 5,782,396 A | 7/1998 | Mastri et al. |
| 5,868,760 A | 2/1999 | McGuckin, Jr. |
| 5,954,259 A * | 9/1999 | Viola et al. .............. 227/176.1 |
| 5,997,510 A | 12/1999 | Schwemberger |
| 6,119,913 A * | 9/2000 | Adams et al. ........... 227/176.1 |
| 6,126,058 A | 10/2000 | Adams et al. |

* cited by examiner

ELECTROMECHANICAL DRIVER DEVICE FOR USE WITH ANASTOMOSING, STAPLING, AND RESECTING INSTRUMENTS

BACKGROUND OF THE INVENTION

1. Field of the Invention

The present invention relates generally to an electromechanical device for use with anastomosing, stapling, and resecting surgical tools, and more specifically to a electromechanical device by which surgical instruments such as anatomosing, stapling, and resecting tools may be remotely actuated.

2. Description of the Prior Art

Upon identification of cancerous or other anomalous tissue in the gastrointestinal tract, surgical intervention is often prescribed. The field of cancer surgery, and more specifically, the surgical procedure by which a section of the gastrointestinal tract which includes cancerous or anomalous tissue is resected, includes a number of uniquely designed instruments. In combination with a description of the present instrumentation and their functions, a description of the state of the art in this surgical procedure shall also be provided.

The first question which must be answered when determining how to treat gastrointestinal cancer relates to the specific location of the cancerous tissue. This is very important insofar as the instruments which are provided in the present art have limitations relating to how far they may be inserted into the gastrointestinal tract. If the cancerous tissue is too far up the colon, for example, then the standard instrumentation provided is unuseable, thus requiring special accomodations. These accomodations generally increase the risk of contamination of the surrounding tissues with bowel contents, increase the length of the surgery and the corresponding need for anaesthesia, and eliminate the benefits of precise anastomosing and stapling which comes from utilizing a mechanized device.

More specifically, in the event that the cancerous tissue is located at a position in the colon which is accessible by the present instrumentation, the patient's abdomen is initially opened to expose the bowel. The surgeon then utilizes a linear cutter and stapling device which cuts the tube of the colon on either side of the cancerous tissue, thereby creating two stapled ends of the bowel (a distal end which is directed toward the anus, and the proximal end which is closest to the small intestine). This is done in order to temporarily minimize contamination.

Figure 1:
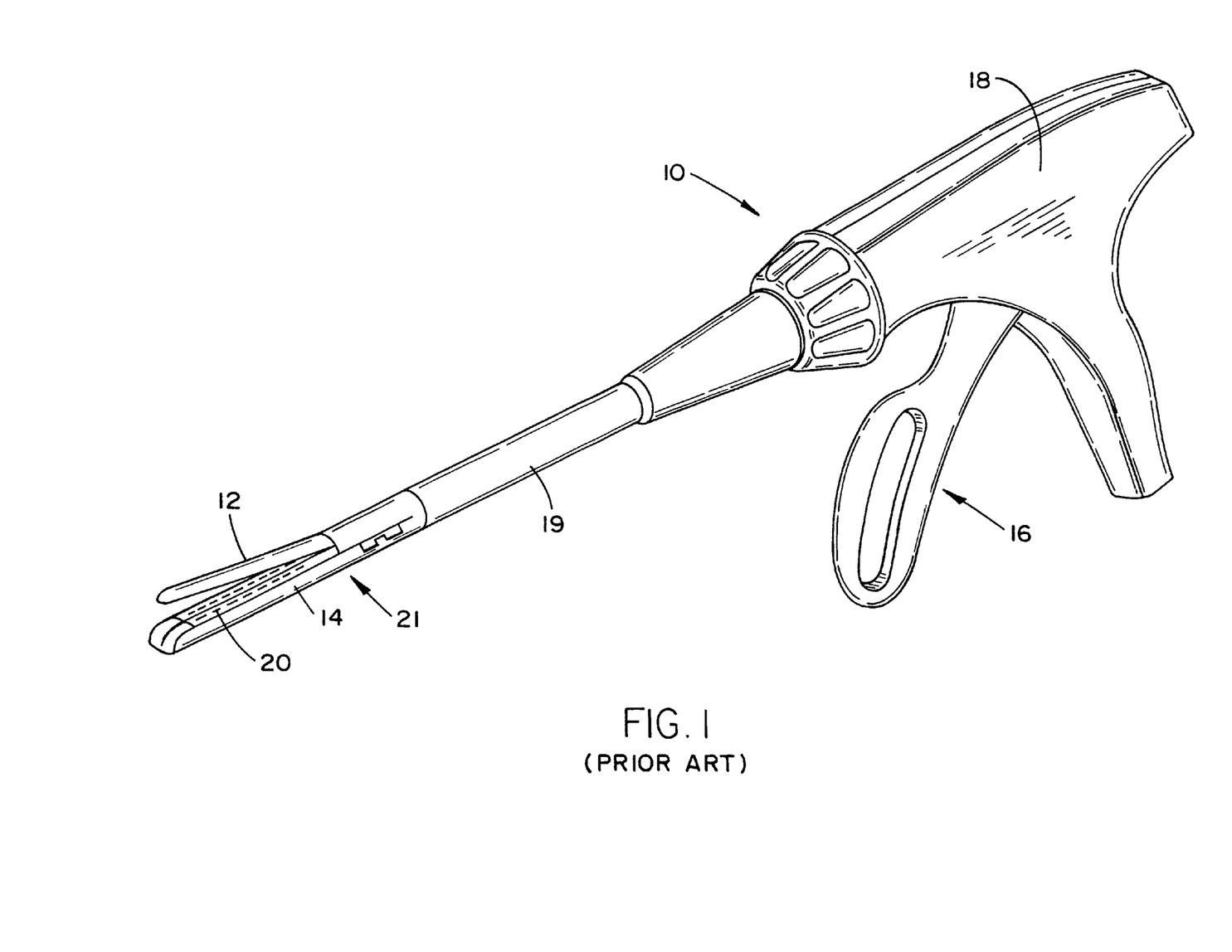
FIG. 1 is a side perspective view of a linear clamping and stapling instrument of the prior art.

More particularly, referring to FIG. 1, the bowel is placed between the scissoring elements 12,14 at the tip of the linear stapling instrument 10. By squeezing the trigger 16 in the handle 18 of the device, the surgeon causes the scissoring elements 12,14 to come together. A second trigger (or a secondary action of the same trigger) is then actuated to drive a series of staples 20 through the clamped end of the colon, thereby closing and transecting the ends.

The surgeon then partially opens the proximal end and inserts the removeable anvil portion of an anastomosing and stapling instrument into the exposed proximal end. This step, as well as those of the remainder of the surgical procedure, are related to the functioning of this surgical instrument. More particularly, and with respect to FIG. 2, the surgeon begins by taking the instrument 30 and manually turning the dial 32 at the base of the handle 34 which causes the anvil head 36 at the opposite end to advance forward.

Figure 2:
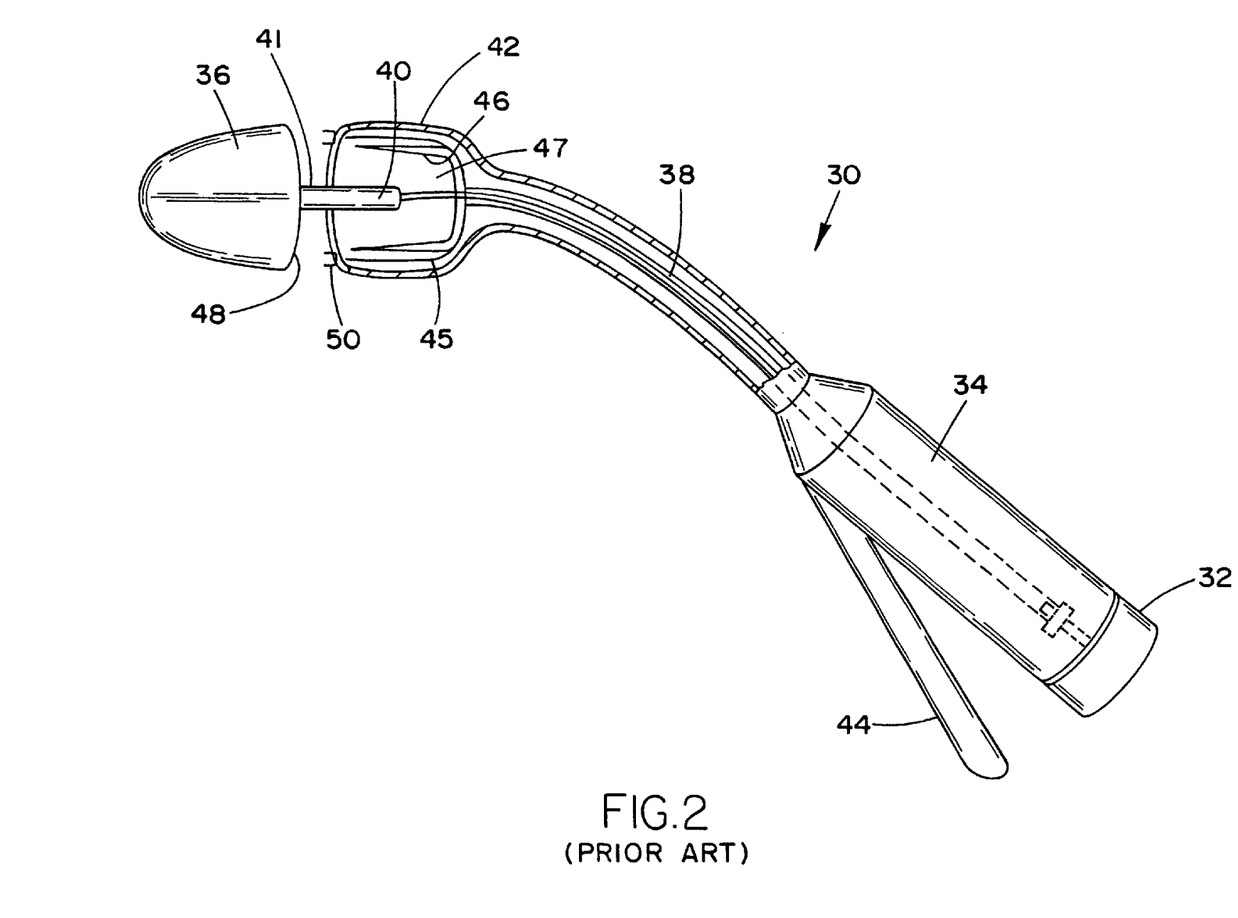
FIG. 2 is a side perspective view of an anastomosing and stapling instrument of the prior art.

The surgeon continues to turn the dial 32 until the anvil head 36 advances to its most extreme extended position. This manual turning requires nearly thirty full rotations. Once fully extended, the anvil head of the instrument is decoupled therefrom and is inserted into the partial opening of the proximal end such that the coupling post extends outwardly therethrough. This partial opening of the proximal end is then sutured closed. The extending shaft 38 of the anastomosing and stapling intrument 30 is then inserted and advanced into the lower colon, transanally, until the coupling stem 40 thereof extends through the stapled distal end. The surgeon then joins the coupling ends of the anvil and shaft together and begins to manually rotate the dial in the handle again, this time bringing the anvil head closer to the end 42 of the shaft.

Once the anvil head and shaft are brought close together, after the surgeon has manually rotated the dial another thirty times, a grip-style trigger 44 in the handle is manually actuated. This actuation causes a circular blade 46 to advance axially out from the tip of the shaft, and into contact with the opposing face 48 of the anvil 36. The blade cuts through the stapled-closed ends of the proximal and distal ends of the colon, thereby also cutting a new pair of ends of the proximal and distal portions of the colon. The tissue which has been severed is held in an interior volume at the end of the shaft.

In lock step with the cutting, the freshly opened ends are joined together by a series of staples 50 which are advanced through holes in the perimeter of the tip of the shaft (being pressed against and closed by the opposing face of the anvil). The coupled shaft and anvil are then withdrawn from the patient.

More particularly with respect to the structural features of the linear stapling instrument 10 of the prior art which is provided in FIG. 1, the device comprises a pistol grip-styled structure 18 having an elongate shaft 19 and distal portion 20. The distal portion includes a pair of scissor-styled gripping elements 12,14 which clamp the open ends of the colon closed. In fact only one of the two scisor-styled gripping elements, the upper jaw portion 12, moves (pivots) relative to overall structure; the other remains fixed. The actuation of this scissoring means (the pivoting of the upper jaw 12 portion) is controlled by means of a grip trigger 16 maintained in the handle. A number of different means have been disclosed for holding the tips of the scissoring arms closed, including snaps, clips, collars, et al.

In addition to the scissoring means, the distal portion also includes a stapling mechanism. The non-moving lower jaw 14 of the scissoring mechanism includes a staple cartridge receiving region and a mechanism for driving the staples 20 up through the clamped end of the colon, against the upper jaw portion, thereby sealing the previously opened end. The scissoring elements may be integrally formed with the shaft, or may be detachable such that various scissoring and stapling elements may be interchangeable.

More particularly with respect to the structural features of the anastomosing and stapling instrument of the prior art which is provided in FIG. 2, the device comprises an anvil portion 36, a staple, blade and reservior portion 42, a shaft portion 38, and a handle portion 34. The anvil portion 36, which is selectively removeable from the tip of the shaft, is bullet shaped, having a blunt nosed top portion, a flat cutting support surface 48 on the bottom, and a coupling post 41 extending axially from the bottom surface.

The staple, blade, and reservior portion 42 (SBR portion) of the instrument is provided at the distal end of the instrument, and includes a selectively advanceable and retractable coupling stem 40 for selectively receiving thereon the anvil portion. This action of the coupling stem is provided by a screw threaded shaft and worming mechanism mounted in the handle 34 (described more fully below). The SBR portion is cylindrical in shape, forming a housing which has a hollow interior. It is this hollow interior which forms the reservior 47. The blade 46 is similarly cylindrical, and seats in the inside of the housing, against the inner wall thereof. The blade is selectively advanceable axially outward from the housing, in accordance with actuation of a trigger 44 mechanism of the handle (again, described more fully below). On the axially outward facing surface of the cylindrical wall of the housing are a series of staple ports, through which the staples 50 of the device are discharged. The same actuation which drives the blade forward similarly drives a series of staple drivers forward within the cylindrical walls. More accurately, the staple driver is a cylindrical component which has a series of protuberances on the axial end thereof, the protuberances being positioned in accordance with the distribution of staples and holes. The staples, prior to being discharged, are mounted in the holes; and they are advanced through the holes by the action of the staple driver and the protuberances thereof.

The shaft portion 38 of the instrument is a simple rigid extended structure which is intended as a sheath for a pair of elongate rods. The first rod is coupled to the worming mechanism introduced above, and described more fully below with respect to the handle portion, and is the means by which the anvil portion and the coupling stem of the SBR portion are selectively advanced and retracted. The second rod is coupled to the trigger 44 of the handle at one end (also introduced above, and described more fully below) and to the blade 46 and staple driver 45 at the other end. The sheath protects the patient and the instrument when it is advanced into the colon transanally. The nature of the actuation mechanisms however, requires that the shaft be rigid. This rigidity limits the length of the shaft 38; and combination, i.e. the length and rigidity of the instrument, these features limit the sections of the colon which may be treated using this device.

The handle 34 of this instrument of the prior art comprises a pistol grip styled structure having a turning dial 32 at the butt (i.e. the end opposing the junction of the shaft portion which the handle) and a finger actuated trigger 44. The trigger includes a safety mechanism which physically prevents actuation unless moved out of the interference position. The turning dial 32 is actionably coupled to a worming mechanism which is used to advance the first rod of the shaft portion (thereby advancing the coupling stem and the anvil 36). The trigger functions as a basic lever to push the second rod forward within the shaft, thereby advancing the blade 46 and staple driver 45.

As with many such devices of the prior art, all of these devices are considered fully disposable, and are, in fact, thrown away after a single use. They are complicated devices, haing multiple moving parts, requiring substantial structural integrity and, therefore, expense in manufacturing. The fact that they are used only once, and no part can be used again render the use of such devices expensive and wasteful of resources.

In addition to this failure, as can be readily observed from the preceeding descriptions, the prior art devices suffer from numerous other limitations which would be desirable to overcome. These include the rigid and limited length shaft of the anastomosing and stapling instrument (which limits the portion of the gastrointestinal tract which may be treated by such a device), as well as the requirement that the surgeon manually actuate a number of different functions (including those associated with the dial and trigger of the anastomosing and stapling instrument and the multiple triggers of the cutting and stapling instrument).

Therefore, it is a principal object of the present invention to provide an instrument for cutting, anastomosing, and stapling, for use in gastrointestinal surgery, which reduces the waste of resources by permitting the reuse of portions thereof.

It is also a principal object of the present invention to provide an instrument which increases the region of the gastrointestinal tract for which it may be used.

It is correspondingly an object of the present invention to provide a gastrointestinal tract surgery instrument assembly which has a flexible shaft component.

It is further an object of the present invention to provide an instrument assembly which reduces the requirements for the surgeon to manually actuate different components and mechanisms.

Other objects of the present invention shall be recognized in accordance with the description thereof provided hereinbelow, and in the Detailed Description of Preferred Embodiments in conjunction with the remaining Figures.

SUMMARY OF THE INVENTION

The preceeding objects of the invention are provided by an electromechanical driver assembly which couples and actuates both a linear stapling attachment and an anastomosing and stapling attachment. It may be recognized by the astute reader that both of the instruments of the prior art, which have been described above, have similar dual actions. More particularly, the linear stapling instrument first clamps and then staples, and the anastomosing and stapling instrument advances and retracts an anvil portion, which is, in effect, a clamping action, and then drives a blade and staples forward. It is, therefore, possible to construct a single common driver assembly which can be used to actuate the functions of each, such that the differing functions may be specific only to attachments, and not to the entirety of the instrument.

More particularly, the present invention comprises three components, which are (1) an electromechanical driver, (2) a linear clamping and stapling attachment, and (3) an anastomosing and stapling attachment, the latter two attachments having a common designed coupling interface which joins with the driver component. It is, however, anticipated that other attachments will be used as well.

First, with respect to the electromechanical driver, the driver has a handle and a flexible drive shaft. The handle has a pistol grip-styled design, having one or more, and preferably two, finger triggers which are independently coupled to at least one, and preferably two separate motors which each turn separate flexible drive shafts (described more fully, hereinbelow). The motors are each dual direction motors, and are coupled to a manual drive switch mounted to the top of the handle, by which the user can selectively alter the turning direction of each motor. This dual direction capacity may be most simply achieved by selecting motors which turn in a direction corresponding to the direction of current, and actuation of the drive switches alters the direction of the current accordingly. In this example, the power source supplying the motors must be a direct current source, such as a battery pack (and most desireably, a rechargeable battery pack). In the event that the device should be useable with an alternating current, either a transformer can be included, or a more sophisticated intermediate gearing assembly may be provided. In conjunction with the present description, the embodiments of the present invention which will be described utilize a rechargeable battery pack providing a direct current.

In addition to the motor components, the handle further includes several other features, including: (1) an remote status indicator; (2) a shaft steering means; and (3) at least one additional electrical supply. First, the remote status indicator may comprise an LCD (or similar read out device) by which the user may gain knowledge of the position of components (for example whether a clamping element is in the proper position prior to the driving of the staples). Second, the handle also includes a manually actuateable steering means, for example, a joystick or track ball, for directing the movement of the flexible shaft (by means of guidewires implanted in the shaft portion described more fully hereinbelow). Finally, the handle may include an additional electrical power supply and an on off switch for selectively supplying electrical power to the attachments.

More particularly, with respect to the flexible shaft, the shaft comprises a tubular sheath, preferably formed of a simple elastomeric material which is tissue compatible and which is sterilizable (i.e. is sufficiently rugged to withstand an autoclave). Various lengths of this shaft may be provided in conjunction with the present invention. In this case, the flexible shaft and the handle portions should be separable. If separable, the interface between the proximal end of the shaft and the distal end of the handle should include a coupling means for the drive components.

Specifically regarding the drive components of the shaft, within the elastomeric sheath are a pair of smaller fixed tubes which each contain a flexible drive shaft which is capable of rotating within the tube. The flexible drive shaft, itself, simply must be capable of translating a torque from the motor in the handle to the distal end of the shaft, while still being flexible enough to be bent, angled, curved, etc. as the surgeon deems necessary to "snake" through the colon of the patient. For example, the drive shafts may comprise a woven steel fiber cable. It shall be recognized that other drive shafts may be suitable for this purpose. In order for the distal end of the drive shaft to couple with an attachment, such as the clamping and stapling device of the present invention (as described more fully below), however, the distal tips of the drive shafts must have a conformation which permits the continued translation of torque. For example, the distal tips of the drive shafts may be hexagonal, thereby fitting into a hexagonal recess in the coupling interface of the attachment. Appropriate gearing mechanisms may be provided at the distal end of the shaft, or in the interfacing portion of the attachment, to ensure that the appropriate torque is provided to the attachment.

As suggested above, in conjunction with the manually actuateable steering means mounted to the handle, the sheath further includes at least two guidewires which are flexible, but are coupled to the inner surface of the sheath near the distal end thereof. The guidewires may be axially translated relative to one another by actuation of the steering means, which action causes the sheath to bend and curve accordingly.

Also as suggested above, in conjunction with the LCD indicator of the handle, the shaft further contains an electrical lead for coupling to the attachments. This electrical lead channels a signal from the attachment to the handle for indicating the status of the attachment (for example, whether a clamping function is holding). Similarly, a second electrical lead may be provided to supply power to separate aspects of the attachment if so required (for example, as will be described more fully with respect to one embodiment of the linear stapling attachment, the use of selectively engageable electromagnetic seal for ensuring continued clamping through the stapling process may be provided and require power selectively provided from the handle's power supply.

More particularly, with respect to the linear clamping and stapling attachment, which has several different potential embodiments, two of which are disclosed herein as examples, the attachment is fitted with two drive extensions, which in operation function as extensions of the flexible drive shafts of the electromechanical driver. That is, when the attachment is mated to the electromechanical driver, the drive extensions are in mechanical communication with the flexible drive shafts such that the activation of the drive shaft motors activates the drive extensions within the linear clamping and stapling attachment. In each embodiment of the attachment, the first drive extension enables a linear clamping mechanism, while the second drive extension enables a stapling mechanism. In one embodiment, the linear clamping mechanism comprises a scissors-cuff system whereby the pivoting upper jaw of the scissors is clamped to the fixed lower jaw of the scissors as a cuff enclosing a length of the scissors is moved from the hinged end of the scissors toward the closing end of the scissors. The scissors can be unclamped as the cuff is returned to its original position. In this embodiment, the first drive extension moves the cuff forward or backward, depending on the turning direction of the corresponding motor in the electromechanical driver.

In a second embodiment, the linear clamping mechanism comprises a separating jaw system whereby an upper jaw is raised and subsequently lowered to meet a lower jaw to effect a clamping. In this embodiment, the first drive extension engages a pair of threaded vertical shafts which raise or lower the upper jaw depending on the turning direction of the corresponding motor in the electromechanical driver.

In each of these embodiments, the stapling mechanism comprises a replaceable tray of open staples set within the lower jaw and a set of corresponding staple guides fitted on the upper jaw, such that when the linear clamping mechanism is in a closed position, the open staples immediately oppose the corresponding staple guides. The stapling mechanism further comprises a wedge pushing system whereby once the linear clamping mechanism is in a closed position, a wedge riding in a channel below the tray of open staples is pushed through the channel. As the wedge moves through the channel, a sloping surface of the wedge pushes the open staples against the corresponding staple guides, thereby closing the staples. After the staples have been closed, the wedge is pulled back through the channel. The second drive extension pushes or pulls the wedge through the channel, depending on the turning direction of the corresponding motor in the electromechanical driver, by engaging a threaded horizontal shaft upon which the wedge, having a matching inner thread, rides.

The distal ends of the scissoring or linearly closing jaws may further include an electromagnetic securing mechanism which serves to hold the distal tips of the jaws together during the stapling step. This is preferred insofar as the action of driving the staples upwardly against the staple guides of the upper jaw may serve to open the jaws. In addition, the electromagnetic securing mechanism may be coupled in electrical communication with the LCD indicator mechanism in the handle (described above) such that the surgeon operating the device may be made aware of when the jaws have closed and the device is in a safe stapledriving position.

Referring now to the anastomosing and stapling attachment, a preferred embodiment is described hereinbelow as a single example of the different variations which could be constructed for the equivalent purpose. As with the linear stapling attachments described above, however, this example demonstrates the universal applicability of the overall electromechanical driver mechanism of the present invention. This attachment comprises an anvil portion, and a staple, blade and reservior portion, which includes a pair of turning drive shafts which are coupleable to the drive components of the shaft element described above, and a corresponding pair of advancing and retracting nuts mounted to the turning drive shafts, but which are prevented from rotating and therefore linearly advance and retract along the shafts when they turn.

The anvil portion includes is bullet shaped, having a blunt nosed top portion, a flat cutting support surface on the bottom, and a freely rotating coupling post extending axially from the bottom surface. This coupling post is designed to be selectively coupleable and removeable from the corresponding nut mounted to one of the turning drive shafts.

The staple, blade, and reservior portion (SBR portion) is cylindrical in shape, forming a housing which has a hollow interior. It is this hollow interior which forms the reservior. On the axially outward facing surface of the cylindrical wall of the housing are a series of staple ports, through which the staples of the device are discharged. A series of staple drivers are mounted within the cylindrical walls, beneath the staple ports, for driving the staples therethrough. More accurately, the staple drivers are a series of protuberances on the outer edge of a single cylindrical component which seats in the wall of the SBR portion. The staples, prior to being discharged, are mounted in the holes; and they are advanced through the holes by the forward motion of the staple driver and the protuberances thereof. The blade is similarly cylindrical, and seats in the inside of the housing, against the inner surface of the wall thereof. Both the blade and the staple driver are mounted to the second nut, which is, in turn, mounted to the other turning drive shaft. As the tuning drive shaft rotates, the nut (which is constrained against rotating) advances along the shaft, thus linearly advancing the blade and staple driver. The blade and the staple driver are, therefore, selectively advanceable axially outward from the housing, in accordance with actuation of the appropriate trigger on the handle.

In a preferred embodiment, the anvil portion and the SBR portion further comprise an electromagnetic sensor mechanism, coupled to the LCD indicator of the handle, which sensor is activated when the two portions have approached each other to the extent necessary for a safe staple firing, whereby the surgeon may have remote knowledge of the state of the attachment disposed within the colon.

In practice, this attachment is utilized, once the section of the colon which is to be removed has been resected (but prior to the linear clamping and stapling step is complete), in the following manner. The surgeon begins by coupling the anastomosing and stapling attachment to the electromechanical driver and advancing the anvil portion to its fullest extent. The anvil head is then removed and inserted into the partially opened proximal end. As described above, this proximal end is then sutured closed. The sugeon then advances the shaft and the SBR portion of the attachment up the colon until it extends through the stapled distal end of the colon. The surgeon then couples the anvil to the advancing and retracting nut of the corresponding drive shaft. Subsequent triggering of the motor in the handle causes the anvil to retract toward the SBR portion. As stated above, in a preferred embodiment, the base of the anvil and the outer edge of the SBR housing comprise an electromagnetic sensor which is coupled to the LCD indicator of the handle, thereby permitting the surgeon to know when the anvil and the SBR have come close enough to drive the blade and staples. Subsequent actuation of the other trigger on the handle causes the corresponding other turning drive shaft to advance the blade and staple driver into contact with the opposing face of the anvil. The blade cuts through the stapled-closed ends of the colon, leaving the tissue which has been severed in the interior reservior. Simultaneous with the cutting, the freshly opened ends are joined together by the series of staples which are advanced through holes in the perimeter edge of the SBR (being pressed against and closed by the opposing face of the anvil). The attachment and the flexible shaft are then withdrawn from the patient.

A DETAILED DESCRIPTION OF THE PREFERRED EMBODIMENTS

While the present invention will be described more fully hereinafter with reference to the accompanying drawings, in which particular embodiments are shown, and with respect to methods of implementation, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 3:
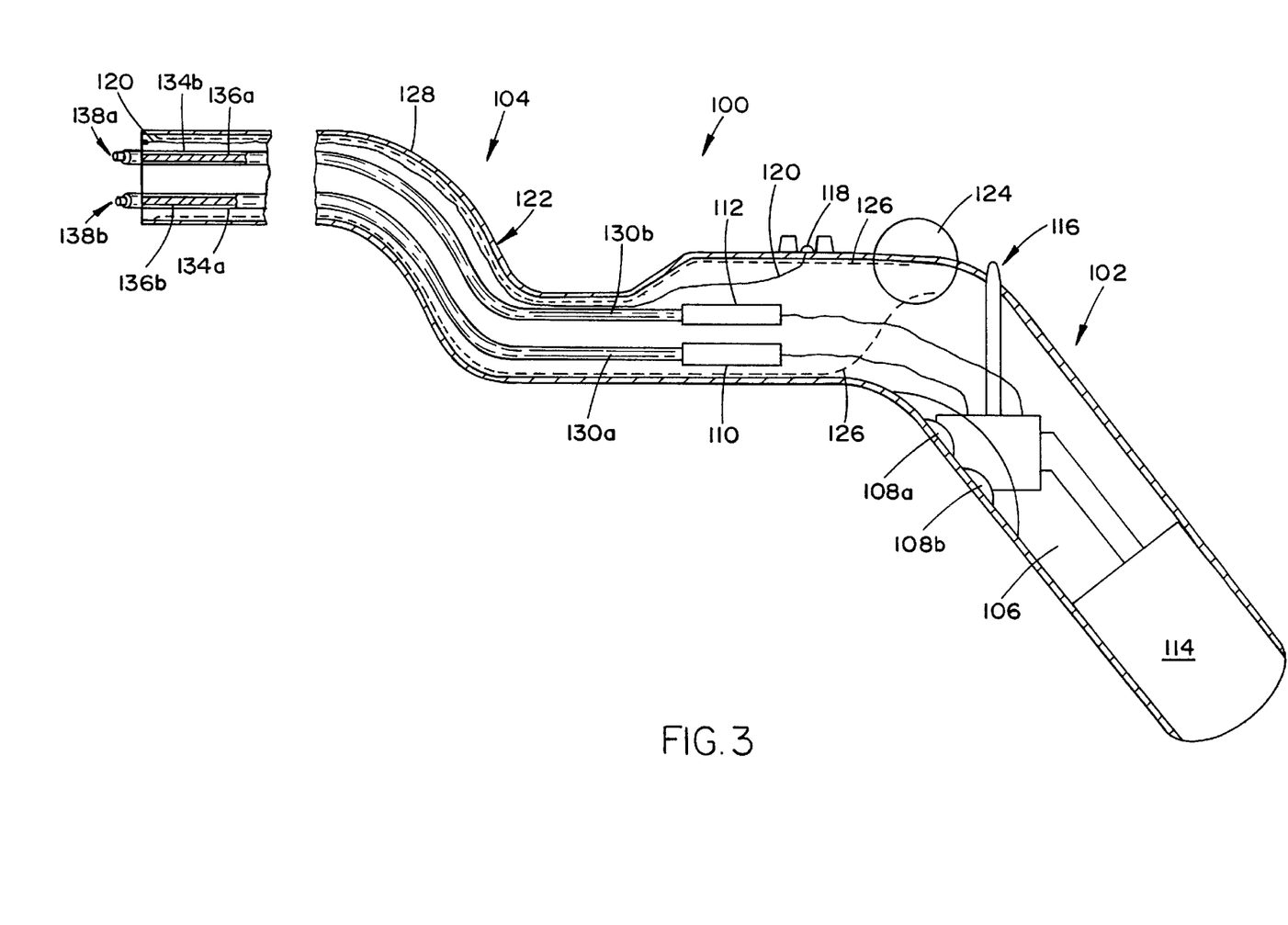
FIG. 3 is a side view of a handle and flexible shaft of the present invention, wherein internal features of the elements are provided in phantom.

More particularly, with respect to the motors 110,112, each is a dual direction motor. In addition to being coupled to the finger actuateable switch, the motors are also each separately coupled to a power source 114 (which is a common source in the present embodiment) and a manual drive switch 116. The manual drive switch 116 is provided on the top of the handle 100, such that the surgeon operator can selectively alter the turning direction of each motor. In the preferred embodiment, the power source 114 supplying the motors 110,112 is a single direct current supplying removeable and rechargeable battery pack. It shall be understood that alternative power sources, including dual direct current sources or single remote alternating current sources (such as the alternating current provided from standard United States 120 Volt, 60 Hertz wall outlets) may be used in conjunction with alternative embodiments. In the event that the driver device should be useable with an alternating current, either a transformer can be included between the motor and the power source, or a more sophisticated intermediate gearing assembly may be provided between the motor and the extended turning drive shaft.

In addition to the motors 110,112 components and the related power and drive switch elements, the handle 100 further includes: (1) a remote status indicator 118 and associated electrical circuit 120; and (2) a manual steering means for causing the remote movement of the distal tip of the flexible drive shaft 122. First, with respect to the remote status indicator 118, in the present embodiment, the indicator means comprises an LCD mounted to the upper portion of the handle. It shall be understood that an equivalent function may be achieved by mounting an audible alarm, or other plain sensory stimulation mechanism, on the handle. The status indicator 118 is coupled to a circuit which extends along the handle and the shaft, and couples to a corresponding electric circuit in the selected attachment (see FIGS. 4–6). The disposition of the attachment, for example in a closed or open position, is associated with the circuit in the attachment being in an open circuit or closed circuit state. The closed circuit state causes the remote status indicator LCD to light up, and in the open circuit state causes the LCD to go out.

Second, the handle also includes a manually actuateable steering means, which in the present embodiment comprises a trackball 124, coupled to a plurality of guidewires 126. The guidewires 126 extend along the flexible shaft portion 122 (described more fully hereinbelow) and are coupled to the tip of the shaft 122. When the trackball 124 is rotated, the guidewires 126 and are pulled, and the tip of the shaft turns correspondingly.

More particularly, with respect to the flexible shaft 122, the shaft comprises a tubular sheath 128 which is formed of a simple, tissue compatible, elastomeric material.

As this device is to be reused, it is important that the material be sterilizable (i.e. is sufficiently rugged to withstand an autoclave). While the embodiment illustrated comprises a contiguous handle 100 and shaft 122, it shall be understood that one having ordinary skill in the art may provide an alternative embodiment having a separable handle and shaft, thus permitting alternative shaft lengths for alternative purposes. In such cases, the flexible shaft 122 and the handle 100 portions should include an interface between the proximal end of the shaft and the distal end of the handle which should include a coupling means for the drive components.

Specifically regarding the drive components 130a,130b of the shaft 122, within the elastomeric sheath 128 are a pair of smaller fixed tubes 134a,134b which each contain a flexible drive shaft 136a,136b which is capable of rotating within the corresponding tube 134a,134b. The flexible drive shaft 122, itself, simply must be capable of translating a torque from the motor in the handle to the distal end 138a,138b of the shaft 122, while still being flexible enough to be bent, angled, curved, etc. as the surgeon deems necessary to "snake" through the colon of the patient. For example, the drive shafts may comprise a woven steel fiber cable, a high tensile strength polymeric material, or a sufficiently flexible unitary metal shaft.

In order for the distal ends 138a,138b of the drive shafts 136a,136b to couple with an attachment, such as the clamping and stapling device of the present invention (see FIGS. 4 and 5), the distal tips 138a,138b of the drive shafts must have a conformation which permits the continued translation of torque. In the present embodiment, this coupling is achieved by a geometric fitting, and more precisely, the distal tips of the drive shafts are hexagonal, and thereby fit into a hexagonal recesses in the coupling interface of the attachment.

In a preferred embodiment, the attachment and the distal end of the shaft should include a collar, or other aligning means, for facilitating the fitting of the attachment onto the distal end of the shaft.

In addition, the tip of the shaft includes the distal ends of the circuit 120 which is coupled to the LCD 118.

Figure 4:
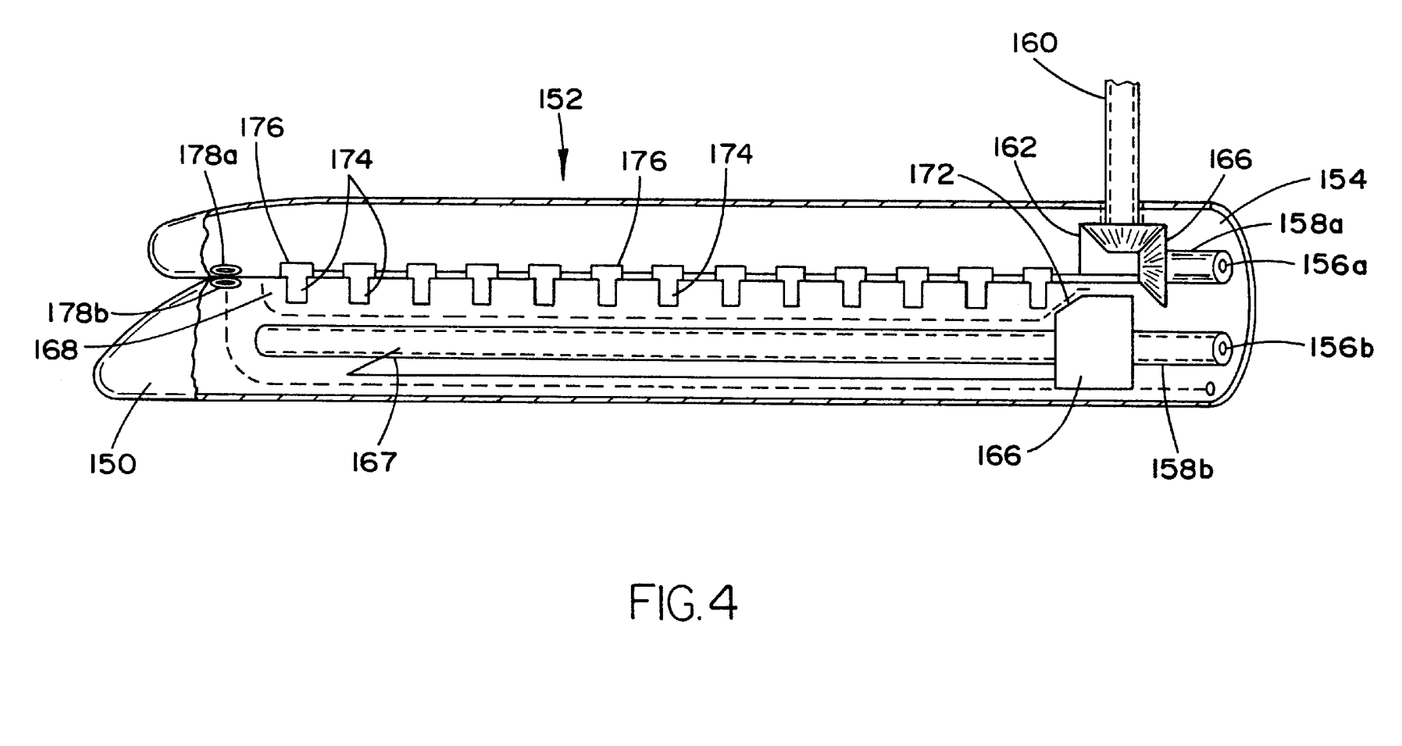
FIG. 4 is a side view of one embodiment of the linear clamping and stapling attachment which is an aspect of the present invention, wherein internal features of the elements are provided in phantom.
Figure 5:
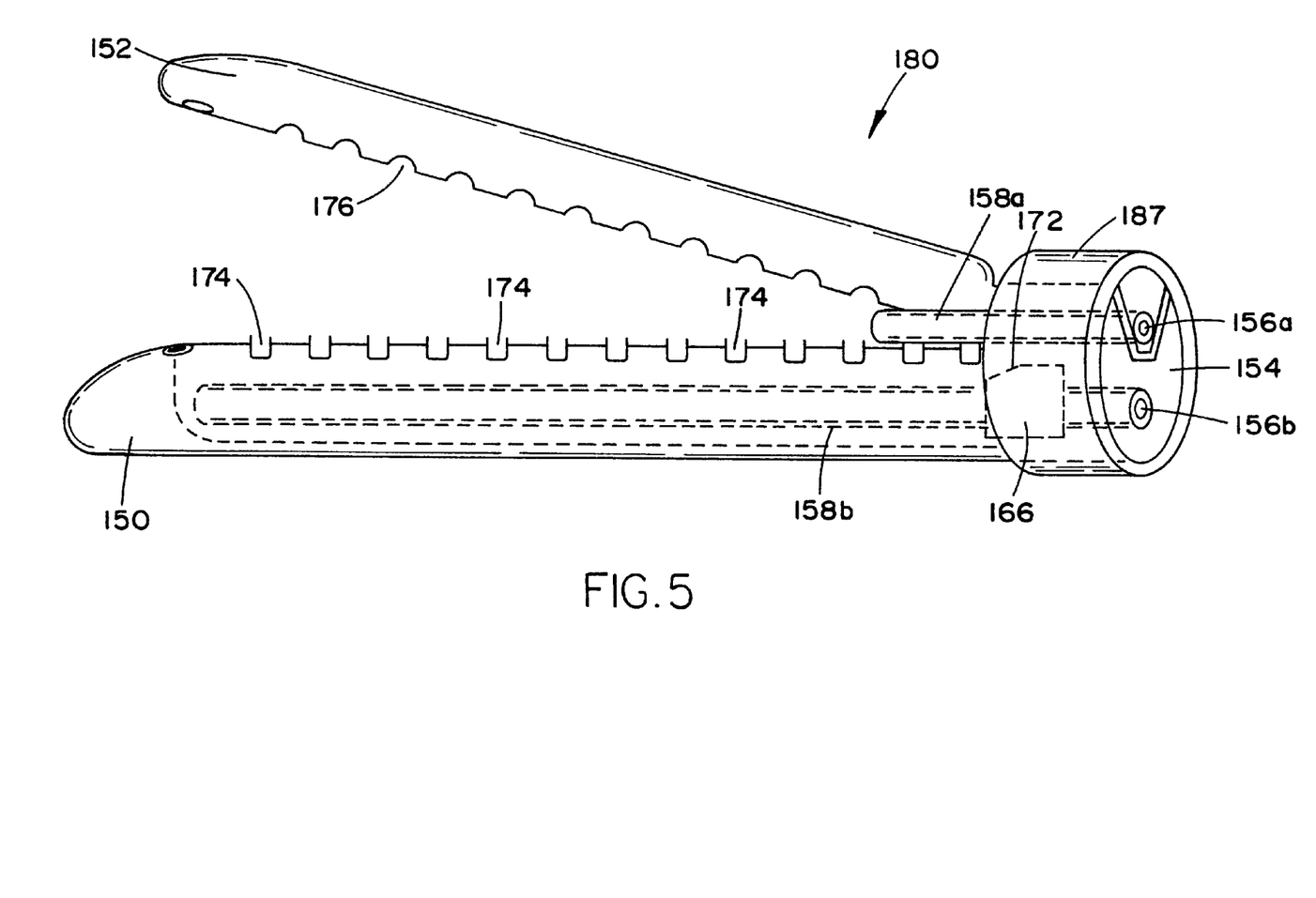
FIG. 5 is a side view of a second embodiment of the linear clamping and stapling attachment which is an aspect of the present invention, wherein internal features of the elements are provided in phantom.

Referring now to FIGS. 4 and 5, two alternative linear clamping and stapling attachments according to the present invention are shown. The first linear clamping mechanism, shown in FIG. 4, comprises a separating jaw system comprising a lower jaw 150 and an upper jaw 152 and a proximal interfacing end member 154. This proximal end member 154 includes two hexagonal shaped sockets 156a,156b into which the distal tips 138a,138b of the drive shafts of the driver device couple. Each of the sockets is formed in the end of a corresponding horizontal turning shaft 158a,158b. The upper horizontal turning shaft 158a is coupled, by means of a transverse gearing member, to a threaded vertical shaft 160 which extends through a correspondingly threaded bore 162 of the upper jaw 152. The upper jaw 152 has a linear track coupling means 169 which corresponds and couples to a linear track 168 formed in the side of the interface end member 154 which is opposite the driver coupling sockets 156a,156b. Subsequent turning of the upper horizontal turning shaft 158a causes the vertical turning shaft 160 to turn. As this shaft 160 turns, the upper jaw 152 rides up and down within the track of the end member 154.

The lower horizontal turning shaft 158b extends axially through the lower jaw 150, which, in turn is fixed to the proximal end member 154. Mounted around this axially extending shaft 158b is a wedge driver mechanism 166 which includes a threaded bore. This wedge driver 166 is locked within a track 167, which prevents the wedge driver 166 from rotating when the shaft 158b turns. Rather, the wedge member 166 rides linearly along the track 167 and along the threading of the shaft 158b. Mounted within a recess 168 in the face of the lower jaw 150 which opposes the upper jaw 152, directly above the wedge driver 166 is a replaceable tray of staples. The wedge driver 166 has a sloped frontal surface 172 which contacts the staple 174 and causes it to be driven upwardly out of the tray 170. When the upper jaw 152 is in close proximity to the lower jaw 150, the staples are closed when they contact the opposing face of the upper jaw 152 (by the action of staple closing guide recesses 176 formed therein).

At the distal tip of the upper and lower jaws are two opposing magnetic sensors 178a,178b, each coupled to a circuit component which mates with the distal ends of the LCD indicator 118 circuit 120. When the jaws come together, the circuit is closed and the LCD indicator is lighted, indicating that the staples may be safely fired.

In operation, the surgeon cuts the tube of the colon on either side of the cancerous tissue, thereby creating two ends of the bowel. The surgeon uses the linear clamping and stapling attachment to temporarily staple the exposed ends. More particularly, the linear clamping and stapling attachment is mated to the distal end of the driver shaft. By manually actuating one trigger (the one which causes the rotation of the upper shaft 136a) the upper jaw 152 opens relative to the lower jaw 150. The open end of the colon is then placed between the jaws 150,152 and the jaws are closed by switching the drive direction for the upper shaft 136a and driving the upper jaw in the opposite direction. The jaws are thereby shut on the end of the colon. At this time the LCD indicator 118 in the handle should light up, indicating that the staples may be safely advanced.

Triggering the second shaft 136b into rotation causes the wedge driver 166 to slide along the track 167 in the lower jaw 150. This drives the staples 174 through the end of the colon and closes them against the staple closing guide recesses 176. The jaws are then reopened and the wedge driver 166 is retracted within the lower jaw 150, the tray 170 of staples 174 is replaced, and the process is repeated for the other open end of the colon.

Referring now to FIG. 5, the second embodiment 180 of the linear clamping and stapling attachment of the present invention is described. In the present embodiment the coupling interface 154 is largely equivalent to the first embodiment inasmuch as the hexagonal ends of the shaft portion are inserted into the corresponding socket ends 156a,156b of the attachment. As before, the shafts of the driver component turn rotating members within the attachment. In this embodiment however, both turning members 158a,158b are horizontal. Mounted to the shaft interfacing member is a fixed lower jaw 150 and a moving upper jaw 152. In this embodiment, the upper jaw 152 is mounted to the lower jaw 150 by means of a spring loaded pivot, which biases the upper jaw into an open disposition relative to the lower jaw. Mounted to the upper turning shaft however, is a linearly tracked cuff 187 which seats around the upper and lower jaw, the advancement of which causes the jaws to come together. The lower jaw includes exactly the same staple 174 tray recess and linearly driven threaded wedge driver 166. Also, the electromagnetic sensor and circuit of the first embodiment is included to indicate to the surgeon when the section of colon has been fully clamped and the staples should be driven.

More particularly, after the surgeon has resected the diseased portion of the colon, the end of the colon is placed between the jaws of the attachment. By actuating the first trigger (and driving the upper shaft), the cuff member 187 advances axially along the outside of the upper and lower jaws 150,152, thus closing the upper jaw onto the colon and lower jaw. Once fully closed, the electromagnetic sensor circuit indicates to the surgeon operator that the staples may be fired, and correspondingly, actuation of the second trigger causes the wedge driver to advance and drive the staples through the colon section. Reverse biasing the motor for the upper turning shaft causes the cuff to retract and the upper jaw to open, thus releasing the now sealed colon end.

Figure 6:
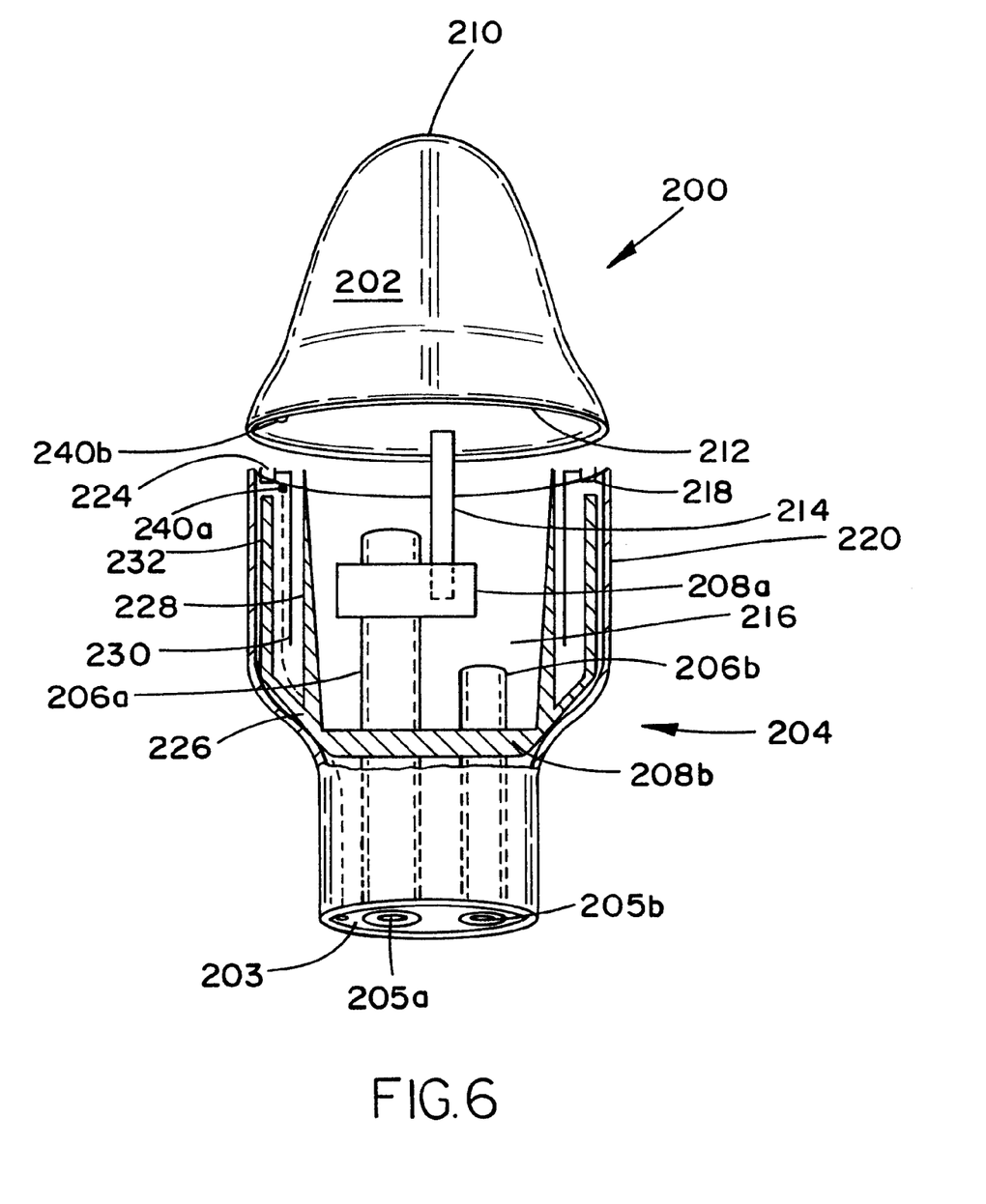
FIG. 6 is a side cut-away view of an anastomosing and stapling attachment which is also an aspect of the present invention.

With reference now to FIG. 6, a preferred embodiment of the anastomosing and stapling attachment 200 is described. This attachment comprises an anvil portion 202, and a staple, blade and reservoir (SBR) portion 204, which includes a pair of turning drive shafts 206a,206b which are coupleable to the drive components 136a,136b of the driver component described above with reference to FIG. 3, and a corresponding pair of advancing and retracting members 208a,208b mounted within tracks and to the turning drive shafts, which are thereby prevented from rotating and therefore linearly advance and retract along the shafts 206a,206b when they turn. More particularly, the base of the SBR portion 204 includes a coupling interface 203 which includes a pair of hexagonal recesses 205a,205b formed in the bases of the threaded turning shafts 206a,206b.

The anvil portion 202 is bullet shaped, having a blunt nosed top portion 210, a flat cutting support surface 212 on the bottom, and a coupling post 214 extending axially from the bottom surface. This coupling post 214 mounts to the first advancing and retracting member 208a which is mounted within a linear track whereby rotation of the shaft 206a causes the member 208a and the anvil 202 coupled thereto to move axially, but not rotationally.

The staple, blade, and reservior portion (SBR) portion 204 is cylindrical in shape, forming a housing which has a hollow interior 216. It is this hollow interior which forms the reservoir. On the axially outward facing surface 218 of the cylindrical wall 220 of the housing are a series of staple ports, through which the staples 224 of the device are discharged. A unitary blade and cylindrical staple driver component 226 is seated within the housing. More particularly, the blade and staple driver component comprises a single element having two concentric cylindrical portions. The blade portion 228 seats within the hollow interior 216, against the interior wall 230 thereof. The staple driver portion 232 seats within the wall 230 of the SBR portion and includes a series of outwardly projecting protuberances which push against staples mounted within the staple ports.

The blade 228 and staple driver portions 232 are coupled at the interior end thereof to a threaded member 208b which seats around turning shaft 206b. The threaded member 208b is constrained within a linear track so that the blade and staple driver are advanced linearly upon rotation of the turning shaft 206b.

In addition, the anvil 202 and the SBR 204 portions each comprise corresponding electromagnetic sensor circuit components 240a,240b which couple to the LCD indicator 118 in the handle.

In practice, this attachment is utilized, once the section of the colon which is to be removed has been resected and stapled shut, in the following manner. The surgeon begins by coupling the anastomosing and stapling attachment 200 to the electromechanical driver and advancing the anvil portion 202 to its fullest extent. The anvil head 202 is then decoupled from the first advancing and retracting member 208 and inserted into the exposed proximal end. As described above, the stapled proximal end of the bowel is then opened partially and the anvil head is inserted. The bowel is then sutured closed. The sugeon then advances the shaft 206a and the SBR portion 204 of the attachment up the colon until it extends through the stapled distal end of the colon. (Alternatively, the surgeon may advance only the flexible shaft up the colon and then reattachment the SBR portion to the distal end once it emerges from the distal end of the bowel.) The surgeon then couples the anvil 202 to the advancing and retracting member 208a by rotation of the corresponding drive shaft 136a. Subsequent reverse biasing and triggering of the same motor in the handle 100 causes the anvil 202 to retract toward the SBR portion 204. Once the electromagnetic sensors 240a,240b mounted on the undersurface of the anvil 202 and the outer edge of the SBR housing come into adjacency sufficient to close the LCD indicator circuit 120, the LCD lightens on the handle. This signals the surgeon operator to trigger the second shafts 136b and 206b into rotation, and advances the staple driver, blade and staples simultaneously. The blade cuts through the stapled-closed ends of the colon, leaving the tissue which has been severed in the interior reservoir. Simultaneous with the cutting, the freshly opened ends are joined together by the series of staples which are advanced through holes in the perimeter edge of the SBR (being pressed against and closed by the opposing face of the anvil). The attachment and the flexible shaft are then withdrawn from the patient.

While there has been described and illustrated new and novel electromagnetic driver mechanisms for use with surgical attachments such as linear clamping and stapling attachments and an anastomosing and stapling attachment, it will be apparent to those skilled in the art that variations and modifications are possible without deviating from the broad spirit and principle of the present invention which shall be limited solely by the scope of the claims appended hereto.

I claim:

1. An electromechanical driver assembly for remotely driving surgical attachments having turning members therein, comprising:
   a flexible shaft including at least two flexible and axially rotating members disposed within the shaft,
   said rotating members having distal and proximal ends,
   each rotating member being capable of transmitting a torque applied to the proximal end thereof, therealong to said distal end thereof,
   said distal ends including means for coupling to said corresponding turning members of said surgical attachments;
   at least one steering wire disposed along the shaft and configured to steer the flexible shaft; and
   a handle portion including
   at least two selectively engageable motors disposed therein and coupled with corresponding ones of said rotating members whereby selective engagement of either of the at least two motors causes the corresponding rotating shaft to rotate, thus transmitting a torque to a corresponding turning member of a surgical attachment.

2. The electromechanical driver assembly as set forth in claim 1, wherein the handle further includes a power source coupled to said at list two motors for independently driving them.

3. The electromechanical driver assembly as set forth in claim 2, wherein the power source is a direct current source.

4. The electromechanical driver assembly as set forth in claim 2, wherein said power source is reversible such that the motors may be reversed biased, thereby driving the motors in the opposite rotational direction.

5. The electromechanical driver assembly as set forth in claim 4, including a manually actuatable switch which is coupled to said power source for selectively reversing the power source.

6. The electromechanical driver assembly as set forth in claim 1, including an actuatable electrical circuit and an indicator means coupled thereto, wherein the actuatable electrical circuit is coupleable to corresponding sensors in said attachment, whereby said indicator means may indicate positions of said attachment in response to the state of the electrical circuit.

7. The electromechanical driver assembly as set forth in claim 6, wherein the indicator means comprises an LCD.

8. The electromechanical driver assembly as set forth in claim 1, wherein the distal ends of the flexible and axially rotating members are hexagonally shaped, and the turning members of the surgical attachment each include corresponding hexagonal sockets, so that the rotating members may couple and transmit torque to the corresponding turning members of the surgical attachment by an interference fit with said turning members.

9. A combined electromagnetic driver and linear clamping and stapling attachment assembly, comprising
   an electromagnetic driver including
   a flexible shaft including at least two flexible and axially rotating members,
   said rotating members having distal and proximal ends,
   each rotating member being capable of transmitting a torque applied to the proximal end thereof, therealong to said distal end thereof,
   said distal ends including means for coupling to said corresponding linear clamping and stapling attachments;
   at least one steering wire disposed along the shaft and configured to steer the flexible shaft; and
   a handle portion, including
   at least two selectively engageable motors disposed therein coupled to corresponding ones of said rotating members of said flexible shaft, whereby selective engagement of either of the at least two motors causes the corresponding rotating shaft to rotate; and
   a linear clamping and stapling attachment including
   an interfacing portion having at least two turning members, each of said turning members being coupleable to one of said at least two flexible and axially rotating members,
   a pair of opposing jaws which are selectively separable and closeable in accordance with the rotation of one of the at least two turning members,
   a plurality of staples and a staple driver mechanism, said staple driver mechanism being selectively coupled in staple driving relation to a second one of the at least two turning members.

10. The electromechanical driver assembly as set forth in claim 9, wherein the handle includes a power source coupled to said at least two motors for independently driving them.

11. The electromechanical driver assembly as set forth in claim 10, wherein the power source is a direct current source.

12. The electromechanical driver assembly as set forth in claim 9, wherein said power source is reversible such that the motors may be reverse biased, thereby driving the motors in the opposite rotational direction.

13. The electromechanical driver assembly as set forth in claim 12, including a manually actuatable switch which is coupled to said power source for selectively reversing the power source.

14. The electromechanical driver assembly as set forth in claim 9, including an actuatable electrical circuit and an indicator means coupled thereto, wherein the actuatable electrical circuit is coupleable to corresponding sensors in said attachment, whereby said indicator means may indicate positions of said attachment in response to the state of the electrical circuit.

15. The electromechanical driver assembly as set forth in claim 14, wherein the indicator means comprises an LCD.

16. The electromechanical driver assembly as set forth in claim 9, wherein the distal ends of the flexible and axially rotating members are hexagonally shaped, and the turning members of the surgical attachment each include corresponding hexagonal sockets, so that the rotating members may couple and transmit torque to the corresponding turning members of the surgical attachment by an interference fit with said turning members.

17. A combined electromagnetic driver and linear clamping and stapling attachment assembly, comprising
   an electromagnetic driver including
   a flexible shaft including at least two flexible and axially rotating members,
   said rotating members having distal and proximal ends,
   each rotating member being capable of transmitting a torque applied to the proximal end thereof, therealong to said distal end thereof,
   said distal ends including means for coupling to said corresponding linear clamping and stapling attachment;
   at least one steering wire disposed along the shaft and configured to steer the flexible shaft; and a handle portion, including
corresponding at least two selectively engageable motors coupled to corresponding ones of said at least two flexible and axially rotating members of said flexible shaft, whereby selective engagement of either of the at least two motors causes the corresponding one of the flexible and axially rotating shaft to rotate; and
an anastomosing and stapling attachment including
an interfacing portion having at least two turning members, each of said turning members being coupleable to one of said at least two flexible and axially rotating members,
an anvil portion which is selectively advanceable and retractable in accordance with the rotation of one of the at least two turning members,
a blade and staple housing portion, selectively coupleable to said anvil portion, which housing portion further includes a blade and staple driver assembly which is coupled to a second one of the at least two turning members such that selective actuation of said second turning member causes said blade and said staple driver to advance out of the housing and toward the anvil portion.

18. An electromechanical driver for driving a surgical attachment, comprising:
an elongated shaft;
at least two axially rotatable drive shafts situated within the elongated shaft, a distal end of each of the drive shafts configured to couple to the surgical attachment to drive the surgical attachment;
at least one steering wire disposed along the elongated shaft and configured to steer the elongated shaft; and
a motor arrangement to drive the drive shafts.

19. The electromechanical driver according to claim 18, wherein the motor arrangement includes a respective motor for each of the drive shafts.

20. The electromechanical driver according to claim 18, wherein the motor arrangement is configured to drive the drive shafts independently of one another.

21. The electromechanical driver according to claim 18, wherein the elongated shaft and drive shafts are flexible.

22. The electromechanical driver according to claim 18, comprising:
a respective trigger corresponding to each of the drive shafts, each respective trigger independently controlling a respective one of the drive shafts.

23. The electromechanical driver according to claim 18, wherein the distal end of each of the drive shafts is configured to be releasably coupled to the surgical attachment.

24. The electromechanical driver according to claim 18, wherein a distal end of the elongated shaft is configured to be coupled to the surgical attachment.

25. The electromechanical driver according to claim 24, wherein the distal end of the elongated shaft is configured to be releasably coupled to the surgical attachment.

26. The electromechanical driver according to claim 18, wherein the distal end of each of the drive shafts is configured to be received in a respective socket of the surgical attachment.

27. The electromechanical driver according to claim 26, wherein the distal end of each of the drive shafts is configured to be releasably received in a respective socket of the surgical attachment.

28. A combined electromechanical driver and a surgical attachment assembly, comprising:
an electromagnetic driver including:
an elongated shaft,
at least two axially rotatable drive shafts situated within the elongated shaft,
at least one steering wire disposed along the elongated shaft and configured to steer the elongated shaft,
a motor arrangement to drive the drive shafts; and
a surgical attachment, a distal end of each of the drive shafts of the electromagnetic driver coupled to the surgical attachment to drive the surgical attachment.

29. The assembly according to claim 28, wherein the surgical attachment includes:
a first jaw;
a second jaw in opposed correspondence with the first jaw, the first and second jaws being relatively movable between an open position and a closed position, a first respective one of the drive shafts effecting the relative movement of the first and second jaws between the open position and the closed position, and a staple driver to drive fasteners through tissue and toward the first jaw, a second respective one of the drive shafts driving the staple driver.

30. The assembly according to claim 28, wherein the motor arrangement includes a respective motor for each of the drive shafts.

31. The assembly according to claim 28, wherein the motor arrangement is configured to drive the drive shafts independently of one another.

32. The assembly according to claim 28, wherein the elongated shaft and drive shafts are flexible.

33. The assembly according to claim 28, comprising:
a respective trigger corresponding to each of the drive shafts, each respective trigger independently controlling a respective one of the drive shafts.

34. The assembly according to claim 28, wherein the distal end of each of the drive shafts is configured to be releasably coupled to the surgical attachment.

35. The assembly according to claim 28, wherein a distal end of the elongated shaft is configured to be coupled to the surgical attachment.

36. The assembly according to claim 35, wherein the distal end of the elongated shaft is configured to be releasably coupled to the surgical attachment.

37. The assembly according to claim 28, wherein the distal end of each of the drive shafts is configured to be received in a respective socket of the surgical attachment.

38. The assembly according to claim 37, wherein the distal end of each of the drive shafts is configured to be releasably received in a respective socket of the surgical attachment.

39. The assembly according to claim 28, wherein the distal end of each of the drive shafts is configured to be received in a respective socket of the surgical attachment.

40. The assembly according to claim 39, wherein the distal end of each of the drive shafts is configured to be releasably received in a respective socket of the surgical attachment.

41. The assembly according to claim 28, wherein the surgical attachment includes:
an axially moveable anvil, a first respective one of the drive shafts effecting the movement of the anvil; and
a staple driver to drive staples through tissue toward the anvil, a second respective one of the drive shafts driving the staple driver.

42. The assembly according to claim 28, wherein the elongated shaft includes a first coupling mechanism and wherein the surgical attachment includes a second coupling mechanism complementary to the first coupling mechanism.

* * * * *